(12) United States Patent
Mirshekari et al.

(10) Patent No.: US 11,600,257 B2
(45) Date of Patent: Mar. 7, 2023

(54) CONNECTOR FOR MECHANICAL WAVEGUIDES

(71) Applicant: Les Solutions Medicales Soundbite Inc., Saint-Laurent (CA)

(72) Inventors: Gholamreza Mirshekari, Sherbrooke (CA); Martin Brouillette, Sherbrooke (CA); Steven Dion, Sherbrooke (CA); Louis-Philippe Riel, Montreal (CA); Chris Karshafian, Toronto (CA); Aaron Ma, Richmond Hill (CA)

(73) Assignee: Les Solutions Medicales Soundbite Inc., Saint-Laurent (CA)

( * ) Notice: Subject to any disclaimer, the term of this patent is extended or adjusted under 35 U.S.C. 154(b) by 928 days.

(21) Appl. No.: 16/349,460

(22) PCT Filed: Nov. 14, 2017

(86) PCT No.: PCT/IB2017/057115
§ 371 (c)(1),
(2) Date: May 13, 2019

(87) PCT Pub. No.: WO2018/087741
PCT Pub. Date: May 17, 2018

(65) Prior Publication Data
US 2020/0193959 A1 Jun. 18, 2020

Related U.S. Application Data

(60) Provisional application No. 62/437,287, filed on Dec. 21, 2016, provisional application No. 62/421,428, filed on Nov. 14, 2016.

(51) Int. Cl.
*G10K 11/24* (2006.01)
*G10K 11/18* (2006.01)
(Continued)

(52) U.S. Cl.
CPC ............. *G10K 11/24* (2013.01); *G10K 11/02* (2013.01); *A61B 17/22012* (2013.01); *A61B 2017/00477* (2013.01); *A61N 7/00* (2013.01)

(58) Field of Classification Search
CPC ........ G10K 11/24; G10K 11/18; G10K 11/02; A61N 7/00; A61B 2017/00477; A61B 2017/0046; B06B 3/04; B06B 1/00
See application file for complete search history.

(56) References Cited

U.S. PATENT DOCUMENTS 2,691,201 A * 10/1954 Matthews ............... B25B 5/103
269/239
4,181,401 A 1/1980 Jensen
(Continued)

FOREIGN PATENT DOCUMENTS

WO 2016170520 A1 10/2016

OTHER PUBLICATIONS

International Search Report; Canadian Intellectual Property Office; International Application No. PCT/IB2017/057115; dated Mar. 2, 2018; 3 pages.
(Continued)

*Primary Examiner* — Edgardo San Martin
(74) *Attorney, Agent, or Firm* — Taft Stettinius & Hollister LLP

(57) ABSTRACT

A connector for connecting together first and second mechanical waveguides, including a first connector body having a first jaw portion provided with a first aperture for receiving the first mechanical waveguide therein, a second connector body having a second jaw portion provided with a second aperture for receiving the second mechanical waveguide therein, with the first and second connector bodies removably securable together, a first mediating body having an acoustic impedance lower than that of the first
(Continued)

mechanical waveguide, with the first mediating body being inserted within the first aperture to be positioned between the first jaw portion and the first mechanical waveguide, and a second mediating body having an acoustic impedance lower than that of the second mechanical waveguide, with the second mediating body inserted within the second aperture to be positioned between the second jaw portion and the second mechanical waveguide.

24 Claims, 7 Drawing Sheets

(51) Int. Cl.
| | |
|---|---|
| *G10K 11/02* | (2006.01) |
| *A61B 17/22* | (2006.01) |
| *A61B 17/00* | (2006.01) |
| *A61N 7/00* | (2006.01) |

(56) References Cited

U.S. PATENT DOCUMENTS

| | | | | |
|---|---|---|---|---|
| 5,022,014 | A | | 6/1991 | Kulczyk et al. |
| 5,044,769 | A | * | 9/1991 | Kulczyk ............... G01K 11/24 374/208 |
| 5,198,894 | A | * | 3/1993 | Hicks .................... A61B 1/042 206/438 |
| 5,792,045 | A | | 8/1998 | Adair |
| 5,960,139 | A | * | 9/1999 | Henning ............... G02B 6/3834 385/60 |
| 5,968,060 | A | * | 10/1999 | Kellogg ............. A61B 17/3476 606/169 |
| 6,140,893 | A | * | 10/2000 | Sciarrino ................ H01P 1/042 333/254 |
| 6,311,010 | B1 | * | 10/2001 | Medeiros ............... G02B 6/266 385/55 |
| 6,567,342 | B1 | | 5/2003 | Purcell et al. |
| 7,393,338 | B2 | | 7/2008 | Nita |
| 7,436,275 | B2 | * | 10/2008 | Dale ....................... H01P 1/042 333/260 |
| 7,764,150 | B2 | * | 7/2010 | Dale ....................... B25B 5/103 333/260 |
| 9,700,339 | B2 | * | 7/2017 | Nield ....................... A61N 7/00 |
| 9,962,064 | B2 | * | 5/2018 | Laser ................. A61B 1/00128 |
| 2014/0005704 | A1 | | 1/2014 | Vakharia et al. |
| 2015/0265305 | A1 | | 9/2015 | Stulen et al. |

OTHER PUBLICATIONS

Written Opinion of the International Searching Authority; Canadian Intellectual Property Office; International Application No. PCT/IB2017/057115; dated Mar. 2, 2018; 4 pages.

European Examination Report, European Patent Office, European Patent Application No. 17869863.5, dated Jul. 18, 2022; 8 pages.

* cited by examiner

CONNECTOR FOR MECHANICAL WAVEGUIDES

CROSS REFERENCE TO RELATED APPLICATIONS

This application is a U.S. National Phase of International PCT Application No. PCT/IB2017/057115 filed Nov. 14, 2017, which claims the benefit of U.S. Provisional Patent Application No. 62/421,428 filed Nov. 14, 2016 and U.S. Provisional Patent Application No. 62/437,287 filed Dec. 21, 2016, the contents of each application hereby incorporated by reference in their entirety.

TECHNICAL FIELD

The present invention relates to the field of mechanical connectors, and more particularly to connectors for connecting together mechanical waveguides.

BACKGROUND

Non-invasive therapies using ultrasound or shock waves are commonly used to treat a variety of medical conditions, such as kidney stones and prostate cancer, for example. They are attractive because the source of mechanical waves is outside the body of the patient to be treated, so the procedure is defined as being not invasive. By the design of the mechanical energy source, this energy is usually focused on a target to be treated within the body. However, there are limitations to this technique. For one, the exact location of the target may be difficult to obtain due to limitations of the imaging method used. Also, the energy may not be focused at the exact desired location due to physical limitations of the focusing wave itself and heterogeneities within the various tissues and organs through which the wave travels. Finally, the energy density at the target may not be sufficient to accomplish the desired treatment.

Therefore there is a need for an improved method and device for better directing and concentrating the mechanical energy produced by an extracorporeal mechanical energy source to achieve better clinical outcomes during medical treatment. This can be achieved by using a mechanical waveguide to transmit the mechanical energy from the extracorporeal mechanical energy source into the body by using a minimally invasive device that can be inserted via a body orifice or blood vessel and directed towards the lesion to be treated.

This minimally-invasive device incorporating a mechanical waveguide needs to be connected to the extracorporeal mechanical energy source via a connector, and ideally this connector should incorporate design and construction features that ensure that energy losses are minimized inside the connector of the minimally-invasive device during operation. In at least some embodiments, it may be required for the connector to ensure a sterile connection between the mechanical waveguide and the energy source.

Therefore, there is a need for an improved mechanical connector for connecting mechanical waveguides.

SUMMARY

According to a first broad aspect, there is provided a connector for connecting together a first mechanical waveguide and a second mechanical waveguide, comprising: a first connector body securable to the first mechanical waveguide, the first connector body comprising a first jaw portion provided with a first aperture for receiving the first mechanical waveguide therein; a second connector body securable to the second mechanical waveguide, the second connector body comprising a second jaw portion provided with a second aperture for receiving the second mechanical waveguide therein, the first and second connector bodies being removably securable together; a first mediating body having an acoustic impedance being lower than an impedance of the first mechanical waveguide, the first mediating body being inserted within the first aperture of the first jaw portion to be positioned between the first jaw portion and the first mechanical waveguide; and a second mediating body having an acoustic impedance being lower than an impedance of the second mechanical waveguide, the second mediating body being inserted within the second aperture of the second jaw portion to be positioned between the second jaw portion and the second mechanical waveguide.

In one embodiment, the first and second mediating bodies each have a respective hole for receiving a respective one of the first and second mechanical waveguides therein.

In one embodiment, the first and second jaw portions each have a tubular shape.

In one embodiment, the first and second mediating bodies each have a tubular shape.

In one embodiment, the first and second mediating bodies each extend along at least a section of a perimeter of a cross-section of a respective one of the first and second mechanical waveguides.

In one embodiment, the first and second jaw portions each extend along at least a section of a perimeter of a cross-section of a respective one of the first and second mediating bodies.

In one embodiment, one of the first and second connector bodies corresponds to a female connector and another one of the first and second connector bodies corresponds to a male connector being securable within the female connector.

In one embodiment, the male and female connectors are each threaded, the male connector being threadingly insertable into the female connector.

In one embodiment, one of the female connector and the male connector is provided with a protrusion and another one of the female connector and the male connector is provided with a recess mating the protrusion for securing the male and female connectors together.

In one embodiment, the second jaw portion is insertable into the first aperture of the first jaw portion so that the second connector body corresponds to the male connector and the first connector body corresponds to the female connector, the connector assembly further comprising a third jaw portion provided with a third aperture for receiving the second mechanical waveguide therein, the third jaw portion being insertable into the second aperture of the second jaw portion.

In one embodiment, an internal face of the second jaw portion is inclined and the external face of the third jaw portion is inclined to mate the internal face of the second jaw portion.

In one embodiment, the first jaw portion is provided with at least one slot longitudinally extending from a distal end thereof.

In one embodiment, the third jaw portion is provided with at least one longitudinally extending slot.

In one embodiment, the first and second mediating bodies are made of a material being at least one of biocompatible and sterilizable.

In one embodiment, the first and second mediating bodies are made of one of rubber and silicon polymer.

In one embodiment, the first and second mediating bodies are each made of an elastic material.

In one embodiment, the connector assembly further comprises mechanical means for laterally aligning a distal end of the first mechanical waveguide and a proximal end of the second mechanical waveguide together.

In one embodiment, the mechanical means comprises an alignment plate comprising an aperture and an inclined plane extending around the aperture, the aperture for receiving therein the distal end of the first mechanical waveguide and the proximal end of the second mechanical waveguide.

In one embodiment, the mechanical means comprises a sleeve insertable over the first and second jaw portions.

In one embodiment, the connector assembly further comprises mechanical means for angularly aligning a distal end of the first mechanical waveguide and a proximal end of the second mechanical waveguide together.

In one embodiment, the connector assembly further comprises mechanical means for exerting an axial compressive force between the first and second mechanical waveguides.

In one embodiment, the mechanical means is adapted to push at least one of the first and second mechanical waveguides towards another one of the first and second mechanical waveguides.

In one embodiment, the mechanical means comprises at least one of a screw, a lever, an inclined plane, a magnet, and a spring.

In one embodiment, the connector assembly further comprises mechanical means for exerting a lateral force on the jaw portions.

In one embodiment, the mechanical means comprises at least one of screws, levers, inclined planes, magnets and springs.

In one embodiment, the first and second mediating bodies are each fixedly secured to the first and second mechanical waveguides, respectively, and to the first and second jaw portions, respectively.

In one embodiment, the connector assembly further comprises at least one of screws and rivets for fixedly securing the first and second mediating bodies to the first and second mechanical waveguides, respectively, and to the first and second jaw portions, respectively.

In one embodiment, the first and second mediating bodies are bonded to the first and second mechanical waveguides, respectively, and to the first and second jaw portions, respectively.

In one embodiment, the first and second mediating bodies are each overmolded to the first and second mechanical waveguides, respectively, and to the first and second jaw portions, respectively.

In one embodiment, the connector assembly further comprises a coupling medium to be positioned between the first and second mechanical waveguides.

In one embodiment, the connector assembly further comprises a sterile barrier for preventing a physical contact between the first and second connector bodies and between the first and second mechanical waveguides.

In one embodiment, the connector assembly further comprises a sterile barrier made of a sterilizable material and insertable between the female and male connectors, the sterile barrier comprising an outer tubular body, an inner tubular body inserted into the outer tubular body, an annular wall extending from a distal end of the outer tubular body to a distal end of the inner tubular body and disk-shaped wall closing a distal end of the inner tubular body, the outer tubular body being positional over an external face of the first jaw portion so that the inner tubular body be insertable into the first aperture of the first jaw portion and the second jaw portion being insertable into the inner tubular body.

In one embodiment, the outer tubular body, the inner tubular body, the annular wall and the disk-shaped wall are integral.

In one embodiment, the sterile barrier is made of a flexible material.

In one embodiment, the sterile barrier is made of a rigid material.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of 1/fc, fc being the center frequency of the mechanical pulse.

In one embodiment, the mechanical pulse has a center frequency fc comprised between about 20 kHz and about 10 MHz. In one embodiment, the amplitude of the mechanical pulse when reaching the distal end of the catheter device is comprised between about 10 MPa and about 1000 MPa. In one embodiment, the duration of the mechanical pulse when reaching the distal end of the catheter device is in the order of 1/fc.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
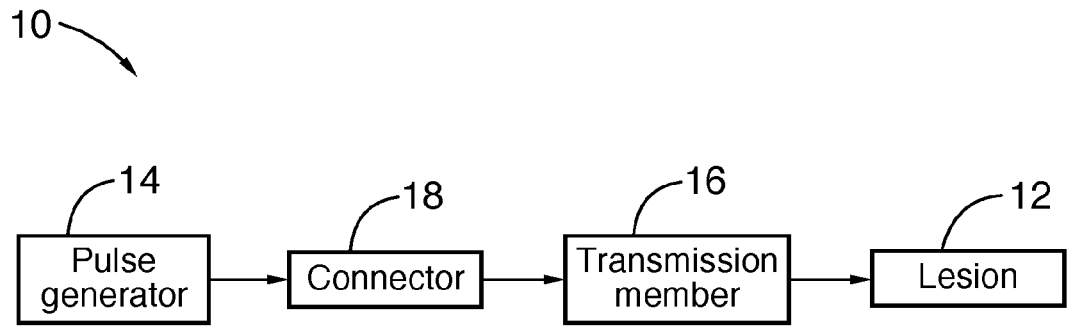
FIG. 1 illustrates a system for generating and delivering mechanical waves or pulses in which a pulse generator is connected to a transmission member via a connector, in accordance with the prior art.

FIG. 1 illustrates one embodiment of a system 10 for treating a lesion 12 present in a blood vessel of a subject, such as an artery, which describes a particular context in which the present connector may be used. The system 10 comprises a pulse generator 14, a connector 18 and a transmission member 16, such as a mechanical waveguide, adapted to propagate mechanical waves and/or pulses.

The pulse generator 14 is adapted to generate mechanical waves, such as high amplitude and short duration pulses. The pulse generator 14 may comprise at least one broadband source and/or at least one narrow band source. The narrow or broad band source may be an electromechanical transducer. The pulse generator 14 may comprise a spatial concentrator to focus the output of at least one source toward a focal zone at which the proximal end of the transmission member 16 is located so as to couple the generated pulse therein.

The transmission member 16 such as a mechanical waveguide extends between a first or proximal end that is operatively connected to the output of the pulse generator 14 via the connector 18 and a second or distal end. The transmission member 16 is adapted to receive mechanical pulses at its proximal end and propagate the mechanical pulses up to its distal end. When it reaches the distal end, the mechanical pulse is at least partially transmitted to generate a transmitted pulse that propagates outside of the transmission member 16. It should be understood that a pulse may also be reflected by the distal end and propagates back in the transmission member 16 towards the proximal end thereof. The transmitted mechanical pulse corresponds to a mechanical pulse that propagates in the medium surrounding the distal end of the transmission member 16 up to the lesion 12. The transmitted pulse further propagates into the lesion 12, which may create cracks within the lesion 12, and eventually cleaves or breaks the lesion 12 into pieces.

In an embodiment in which the distal end of the transmission member 16 is adapted to abut against the lesion 12, the transmission member 16 may further be used to break the lesion 12 and/or drill a hole into the lesion 12. The transmission of the mechanical pulse at the distal end of the transmission member 16 creates a movement of the distal end of the transmission member 16. This movement may be along the longitudinal axis of the transmission member 16. Alternatively, the movement may be perpendicular to the longitudinal axis or it may be a combination of movements both along the longitudinal axis and perpendicular to the longitudinal axis of the transmission member. During this movement, the distal end of the transmission member 16 nominally first moves towards the lesion 12 and then moves back into its initial position. It should be understood that the movement may be inverted (i.e., the distal end may first move away from the lesion 12 and then towards the lesion 12) depending on the polarity of the mechanical pulse reaching the distal end of the transmission member 16. When a plurality of distinct mechanical pulses are successively transmitted at the distal end of the transmission member 16, the movement of the distal end may be seen as a jack-hammer movement which may be used to treat the lesion 12.

The connector 18 allows removably or non-permanently connecting the proximal end of the transmission member 16 to the pulse generator 14 and is used to ensure that the mechanical pulses generated by the pulse generator 14 are efficiently transmitted into the transmission member 16 while allowing disconnection of the transmission member 16 from the pulse generator 14 as desired.

Figure 2:
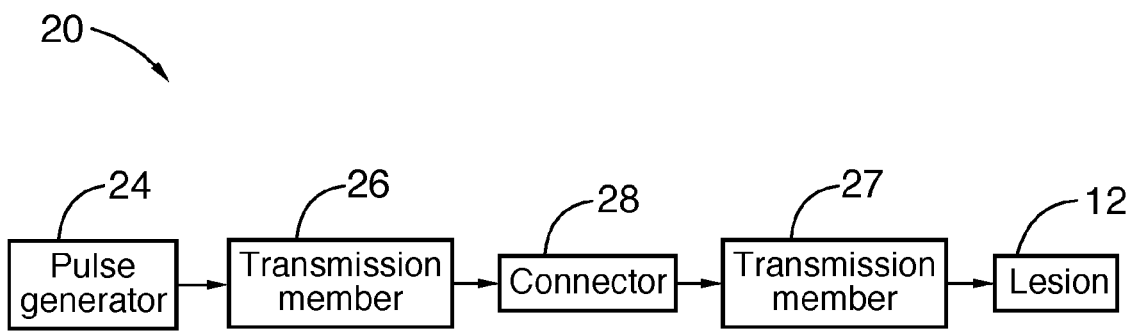
FIG. 2 illustrates a system for generating and delivering mechanical waves or pulses in which two transmission members are connected together via a connector, in accordance with the prior art.

FIG. 2 illustrates another embodiment of a system 20 for treating a lesion 12 which describes a different context in which the present connector is to be used. The system 20 comprises a pulse generator 24, transmission members or mechanical waveguides 26 and 27 each adapted to propagate mechanical waves or pulses, and a connector 28. The connector 28 is used to removably or non-permanently connect the distal end of the mechanical waveguide 26 to the proximal end of the transmission member 27 in order to propagate mechanical pulses or waves coming from the mechanical waveguide 26 into the mechanical waveguide 27. As result, when the connector 28 is installed between the mechanical waveguides 26 and 27, mechanical waves or pulses generated by the pulse generator 24 and propagating in the mechanical waveguide 26 can be coupled into the mechanical waveguide 27. The connector 28 further allows disconnection of the first transmission member 26 from the second transmission member 27 as desired. It should be understood that the system 20 may comprise a further connector for connecting together the pulse generator 24 and the transmission member 26.

Figure 3:
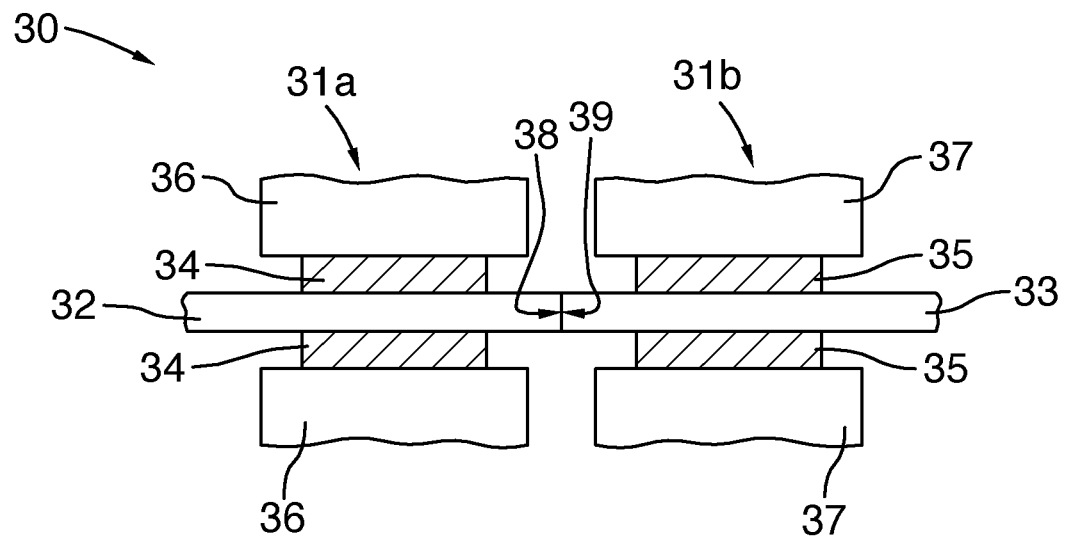
FIG. 3 schematically illustrates a connector for connecting together two mechanical waveguides, in accordance with a first embodiment.

FIG. 3 schematically illustrates a connector 30 that can be used as connector 18 or 28 to connect a first element 32, e.g., the output of a pulse generator or a first mechanical waveguide, to a second mechanical waveguide 33. It should be understood that the output of the pulse generator may be considered as a mechanical waveguide.

The connector 30 comprises a first connector body 31a to be installed on the first element 32 and a second connector body 31b to be installed on the mechanical waveguide 33. The first and second connector bodies 31a and 31b are shaped and sized so as to removably securable together in order to connect the element 32 to the mechanical waveguide 33. It should be understood that the connector bodies 31a and 31b may be provided with any adequate design which allows them to be removably securable together. For example, the connector body 31a may be a female connector and the connector body 31b may be a male connector adapted to be screwed into the connector body 31a. In another example, the connector body 31b may be inserted into the connector body 31a which may be clamped over the connector body 31b. In another example, the connector bodies 31a and 31b may be permanent magnets, electromagnets and/or ferromagnetic bodies to ensure a removable connection between the two.

The first connector body 31a comprises a jaw portion 36 which defines an aperture in which the first element 32 such as the distal portion of a mechanical waveguide is received while the second connector body 31b comprises a jaw portion 37 which defines an aperture in which the proximal portion of a mechanical waveguide 33 is received. The jaw portion 36 extends along at least a portion of the perimeter of the cross-section of the element 32 while the jaw portion 37 extends along at least a portion of the perimeter of the cross-section of the mechanical waveguide 33.

The connector 30 further comprises a first mediating body 34 and a second mediating body 35 each made of a material having a low acoustic impedance, defined as the product of density and speed of sound, i.e., an acoustic impedance being lower than that of the mechanical waveguide 32, 33, respectively, and/or of an elastic material so as to minimize or at least reduce coupling losses between the mechanical waveguide 32, 33 and the connector 30. In the same or another embodiment, the first mediating body 34 and a second mediating body 35 each made of an elastic material so as to minimize or at least reduce coupling losses between the mechanical waveguide 32, 33 and the connector 30. The first and second mediating bodies 34 and 35 each comprise a longitudinal aperture extending therethrough for receiving a respective mechanical waveguide 32, 33 therein. The first mediating body 34 is inserted into the aperture of the jaw portion 36 so as to be positioned between the jaw portion 36 and the element 32 when the element 32 is received within the jaw portion 36. The second mediating body 35 is inserted into the aperture of the jaw portion 37 so as to be positioned between the jaw portion 37 and the mechanical waveguide 33 when the mechanical waveguide 33 is received within the jaw portion 37.

The mediating body 34, 35 allows for isolating the element 32 or the mechanical waveguide 33 from the jaw portion 36, 37 or at least reduce the surface area of contact between the element 32 or the mechanical waveguide 33 and the jaw portion 36, 37, thereby reducing the coupling of mechanical waves from the element 32 to the jaw portion 36 and from the mechanical waveguide 33 to the jaw portion 37. As a result, the coupling losses are reduced.

In one embodiment, the mediating bodies 34 and 35 may have adhesion properties that allow them to be bond to the surfaces of their respective jaw portion 36, 37 and their respective mechanical waveguide 32, 33 to enhance the axial force of connection.

It should be understood that the jaw portion 36, 37 may have any adequate shape. For example, the jaw portion 36, 37 may be tubular. In another example, the jaw portion 36, 37 may have an external rectangular or square cross-section and its internal aperture may also be rectangular or square. In one embodiment, the jaw portion 36, 37 may extend along the whole circumference of the mediating body 34, 35 or the mechanical waveguide 32, 33. In another embodiment, the jaw portion 36, 37 may extend only along a section of the circumference of the mediating body 34, 35 or the mechanical waveguide 32, 33.

Similarly, the mediating bodies 34 and 35 may have any adequate shape and size. For example, the mediating body 34, 35 may be tubular. In another example, the external face of the mediating body 34, 35 may have a shape that matches that of the aperture of the jaw portion 36, 37 and the internal face of the mediating body 34, 35 may have a shape that matches that of the mechanical waveguide 32, 33. In one embodiment, the mediating body 34, 35 may extend along the whole circumference of the mechanical waveguide 32, 33. In another embodiment, the mediating body 34, 35 may extend only along a section of the circumference of the mechanical waveguide 32, 33.

While the first and second connector bodies 31a and 31b are secured together, the distal end 38 of the element 32 is at the same time brought into physical contact with the proximal end 39 of mechanical waveguide 33, thereby allowing the propagation of mechanical waves between the two mechanical waveguides 32 and 33. Once the first and second connector bodies 31a and 31b are connected together, an axial force, in the direction of the longitudinal axis of both waveguides 32 and 33, is applied continuously to the distal end 38 of the element 32 and to the proximal end 39 of the mechanical waveguide 33 to ensure that the distal end 38 and proximal end 39 abut one against the other and are maintained in a state of axial compression at all time during use of the connector 30. This axial force is applied through the jaw portions 36, 37 of the connector 30.

It should be understood that any adequate means may be used for fixedly and removably secure the first and second connector bodies while generating an axial force of the ends 38 and 39 of the elements 32 and 33 to be connected together. For example, the first connector body 31a may be a threaded male connector and the second connector body 31b may be a threaded female connector. By screwing the male connector into the female connector, the two elements 32 and 33 are connected together and an axial force is exerted on their two ends 38 and 39 so that the ends 38 and 39 firmly abut one against the other.

In one embodiment, the connector 30 or at least some of its components is made of sterilizable material(s).

In one embodiment, the mediating bodies 34 and 35 may be made of an electrically isolating material that allows for electrical isolation of the mechanical waveguides 32 and 33 from the jaw portions 36 and 37.

In one embodiment and as typical mechanical waveguides 32, 33 are made from metallic materials such as steel, aluminum, titanium or titanium alloy(s), the mediating bodies 34, 35 may be made of rubber, silicon polymer and other soft and flexible material, for example. In one embodiment the mediating bodies 34, 35 have made of an elastic material. In one embodiment the mediating bodies 34, 35 are made of an elastic material. In one embodiment the mediating bodies 34, 35 are electric insulators. In one embodiment, the mediating bodies 34, 35 are biocompatible and sterilizable.

In one embodiment and in addition to provide good energy transmission, the connector 30 may also incorporate other functions. First, it may comprise mechanical features that ensure good alignment between the longitudinal axis of the distal end 38 of the mechanical waveguide 32 and that of the proximal end 39 of the mechanical waveguide 33. Second it may comprise mechanical features that ensure good angular alignment between the face of the distal end 38 of the element 32 and the face of the proximal end 39 of the mechanical waveguide 33. Furthermore, it may comprise mechanical features that provide sufficient axial compressive force between the face of the distal end 38 of the first element 32 and the face of the proximal end 39 of the mechanical waveguide 33.

The aforementioned compressive force requirement at the distal end 38 and the proximal end 39 can be satisfied, for example, by pushing a moveable proximal end 39 into a stationary distal end 38. The pushing force can be achieved by using any adequate means such as a screw, a lever, an inclined plane in contact with the jaw portion 37 or a combination thereof. This pushing force can also be achieved by using springs or static, electrically-actuated or permanent magnets mounted on the jaws portions 36, 37 and facing each other.

The compressive force requirement can also be satisfied, for example, by pushing a moveable distal end 38 and a moveable proximal end 39 towards one another. This pushing can be achieved in the same manner as above, with the mechanism now in contact with both jaws 36, 37.

Figure 4:
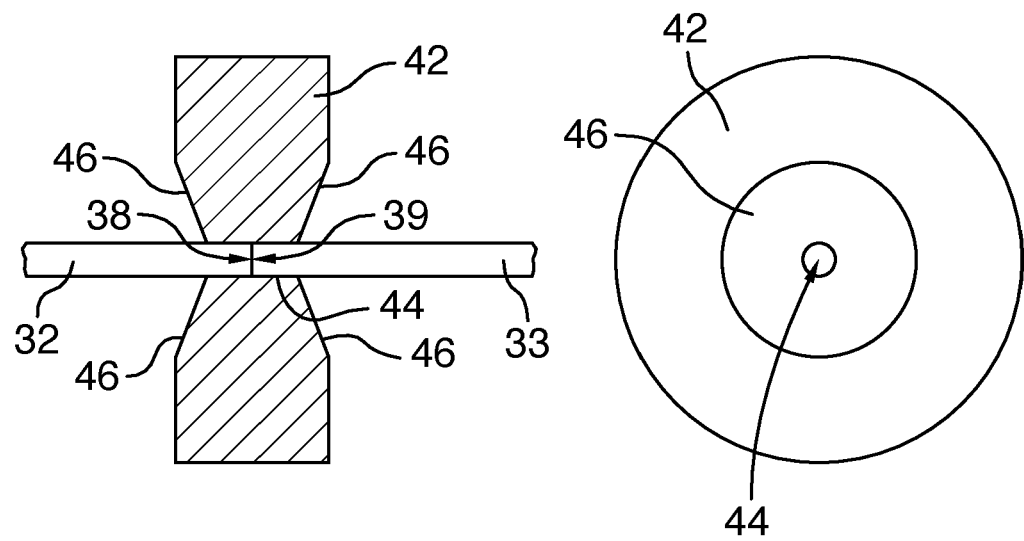
FIG. 4 illustrates an alignment plate for aligning mechanical waveguides, in accordance with an embodiment.

As shown in FIG. 4, the axial and face alignment requirements can be satisfied, for example, by using an alignment plate 42 provided with opposite inclined planes 46 and an orifice 44 having the same cross-section shape and dimensions as those of the distal end 38 of the first mechanical waveguide 32 and the proximal end 39 of the second mechanical waveguide 33. The inclined planes extend around the aperture 44 on opposite sides thereof and are inwardly oriented towards the center of the aperture 44. The alignment plate 42 is contained within the connector 30 between the first and second connector bodies and at least one of the connector bodies 30a and 30b may be movable relative to the alignment plate 42. As they move towards one another by securing the first and second connector bodies 30a and 30b to one another, the distal end 38 of the element 32 and the distal end 39 of the mechanical waveguide 33 each abut a respective inclined plane 46 and slide along their respective inclined plane 46 towards the aperture 44 before penetrating into the aperture 44 and abutting one against the other. The inclined planes 46 act as guiding elements for guiding the ends 38 and 39 towards the aperture 44.

The aperture 44 may have any adequate length. In one embodiment, the length of the aperture 44 is not too long to prevent mechanical energy losses by contact of the mechanical waveguides 32 and 33 with the alignment plate 42 within the aperture 44.

In one embodiment, the alignment plate 42 may be made of a material that has a low acoustic impedance to reduce the coupling loss. In the same or another embodiment, the alignment plate 42 may be made of an electrically isolating material to electrically isolate the waveguides 32 and 33.

In one embodiment, the axial and face alignment requirements can also be satisfied, for example, by using a male/female arrangement whereby the jaw portion 36 is the female member and the jaw portion 37 is the male member, or vice-versa.

In another embodiment, if the jaws portions 36, 37 have the same outside dimensions d1, then proper alignment can be ensured by using an external sleeve that has essentially the same inside dimension d2 as the outside dimension d1.

With soft and flexible mediating bodies 34 and 35 intervening between the jaw portions 36 and 37 and the mechanical waveguides 32 and 33, respectively, and upon application of the axial force to ensure that the connection is constantly in axial compression, it may be possible that slippage between the jaw portions 36, 37, the mediating body 34, 35 and the mechanical waveguide 32, 33 occurs. In order to prevent this slippage, the mediating bodies 34 and 35 should be prevented from moving axially relative to their respective jaw portion 36, 37, and the mediating bodies 34 and 35 should also be prevented from moving axially relative to their respective mechanical waveguides 32, 33. In one embodiment, this can be achieved by fixedly attaching the mediating bodies 34 and 35 to their respective jaw portion 36, 37 and their respective mechanical waveguide 32, 33. This can be performed, for example, by bonding, screwing or riveting the mediating bodies 34, 35 to their respective jaw portion 36, 37 and to their respective mechanical waveguide 32, 33. In another example, this can also be performed by overmolding the mediating layers 34, 35 on their respective jaw portion 36, 37 and their respective mechanical waveguide 32, 33. It should be understood that a combination of at least two of the above-described methods for fixedly attaching the mediating bodies 34 and 35 to their respective jaw portion 36, 37 may be used.

In another embodiment, slippage can be prevented by relying on static friction between the components, where it is known that the friction force is proportional to the normal force between the components. To increase the friction force it is therefore possible to apply a lateral force on the jaw portions 36 and 37 such that the mechanical waveguides 32 and 33 are laterally squeezed between their corresponding mediating bodies 34 and 35 by their corresponding jaw portions 36 and 37. This lateral force can be provided by screws, levers, inclined planes or any combination thereof. This lateral force can also be provided by magnets or springs.

It should be understood that slippage can be prevented by using any combination of the above-described methods. For example, the mediating bodies 34 and 35 may be fixedly secured to their corresponding jaw portion 36, 37 and a lateral force may be applied to the jaws portions 36 and 37 to also rely on friction between the mechanical waveguides 32 and 33 and their corresponding mediating bodies 34 and 35.

In an embodiment in which friction is relied upon to prevent slippage between the waveguide 32, 33, the mediating body 34, 35 and/or the jaw portion 36, 37, it may be possible to modulate the friction force between these components by varying the lateral force. In one embodiment, the lateral force is applied to ensure the connection between the mechanical waveguides 32, 33 during use, while the lateral force is removed to eliminate friction, which may allow the removal of one or both mechanical waveguides 32 and 33 from the connector 30, when not in use.

Figure 5:
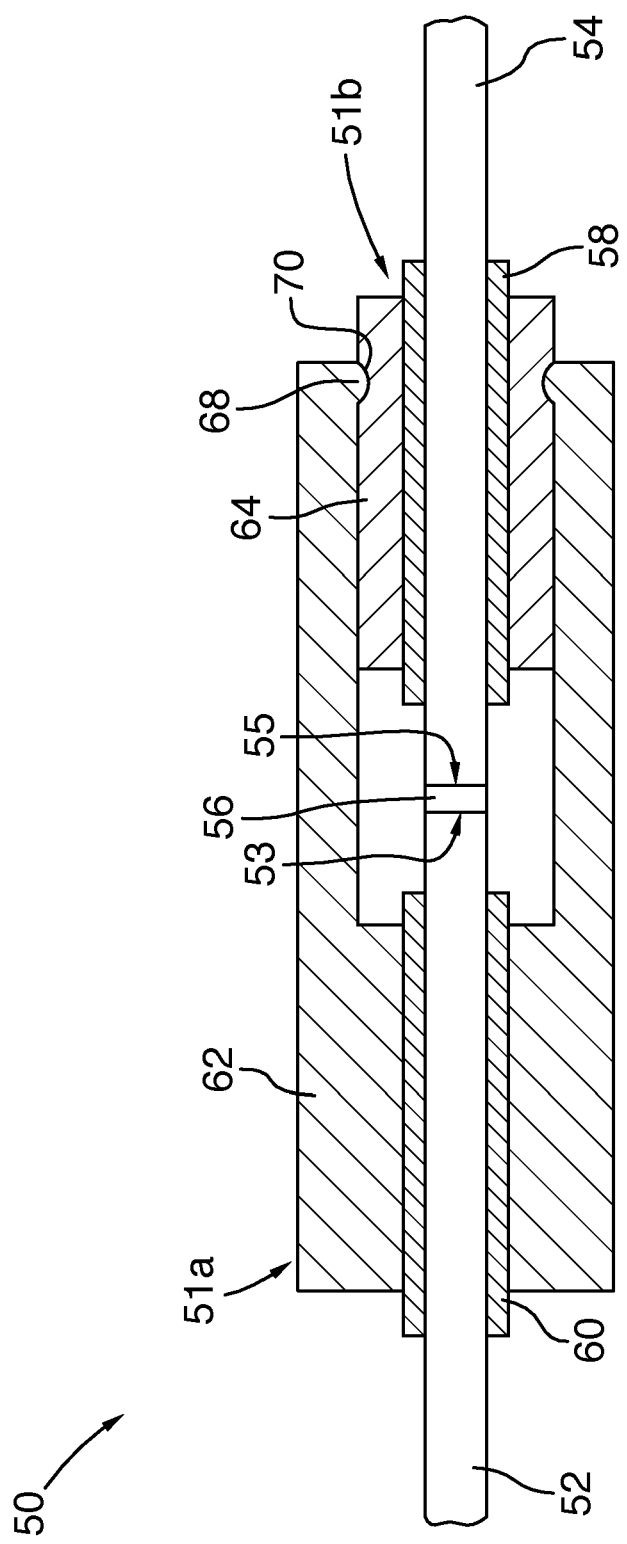
FIG. 5 is a cross-sectional view of a connector assembly comprising a female connector body and a male connector body insertable into the female connector body for coupling together two mechanical waveguides, in accordance with an embodiment.

FIG. 5 schematically illustrates one embodiment of a connector assembly 50 that can be used as connector 18 or 28 to connect a first element 52, e.g., the output of a pulse generator or a first mechanical waveguide, to a second mechanical waveguide 54. It should be understood that the output of the pulse generator may be considered as a mechanical waveguide.

The connector assembly 50 comprises a first connector body 51a to be installed on the first element 52 and a second connector body 51b to be installed on the mechanical waveguide 54. The first and second connector bodies 51a and 51b are removably securable together in order to non-permanently connect the element 52 to the mechanical waveguide 54 and allow the propagation of mechanical waves or pulse between the element 52 and the mechanical waveguide 54. The first connector body 51a comprises a first jaw portion 62 which defines a first aperture in which the first element 52 is received while the second connector body 51b comprises a second jaw portion 64 which defines a second aperture in which the mechanical waveguide 54 is received. The jaw portion 62 extends along at least a portion of the perimeter of the cross-section of the element 52 while the jaw portion 64 extends along at least a portion of the perimeter of the cross-section of the mechanical waveguide 54.

The connector assembly 50 further comprises a first mediating body 60 and a second mediating body 58 each made of a material having an acoustic impedance lower than that of their respective mechanical waveguide 52, 54 so as to minimize or at least reduce coupling losses between the mechanical waveguides 52 and 54 and the connector assembly 50. The first and second mediating bodies 60 and 58 each comprise a longitudinal aperture extending therethrough for receiving a respective mechanical waveguide 52, 54 therein. The first mediating body 60 is inserted into the aperture of the jaw portion 62 so as to be positioned between the jaw portion 62 and the element 52 when the element 52 is received within the jaw portion 62. The second mediating body 58 is inserted into the aperture of the jaw portion 64 so as to be positioned between the jaw portion 64 and the mechanical waveguide 54 when the mechanical waveguide 54 is received within the jaw portion 64.

In one embodiment, the mediating bodies 60 and 58 may be made of an elastic material to reduce coupling losses. In the same or another embodiment, the mediating bodies 60 and 58 may be made of an electrically isolating material.

The mediating bodies 58 and 60 allow for isolating the element 52 and the mechanical waveguide 54, respectively, from the jaw portions 62 and 64, respectively, or at least reduce the surface area of contact between the element 52 and the mechanical waveguide 54, respectively, and the jaw portions 62 and 64, respectively, thereby reducing the coupling of mechanical waves from the element 52 to the jaw portion 62 and from the mechanical waveguide 54 to the jaw portion 64. As a result, the coupling losses are reduced.

In this embodiment, the jaw portions 62 and 64 mate into each other in a male-female arrangement. It should be understood that the jaw portion 62, 64 may have any adequate shape to allow this mating. For example, the jaw portion 62, 64 may be tubular. In another example, the jaw portion 62, 64 may have an external rectangular cross-section and its aperture may also be rectangular. In one embodiment, the jaw portion 62, 64 may extend along the whole circumference of the mediating body 58, 60 or the mechanical waveguide 52, 54. In another embodiment, the jaw portion 62, 64 may extend only along the section of the circumference of the mediating body 58, 60 or the mechanical waveguide 52, 54.

Similarly, the mediating bodies 58 and 60 may have any adequate shape and size. For example, the mediating body 50, 60 may be tubular. In another example, the external face of the mediating body 58, 60 may have a shape that matches that of the aperture of the jaw portion 62, 64 and the internal face of the mediating body 58, 60 may have a shape that matches that of the mechanical waveguide 52, 54. In one embodiment, the mediating body 58, 60 may extend along the whole circumference of the mechanical waveguide 52, 54. In another embodiment, the mediating body 58, 60 may extend only along the section of the circumference of the mechanical waveguide 52, 54.

While the first and second connector bodies 51a and 51b are secured together, the distal end 53 of the element 52 is concurrently brought into physical contact with the proximal end 55 of mechanical waveguide 54, thereby allowing the propagation of mechanical waves between the element 52 and the mechanical waveguide 54.

The first and second connector bodies 51a and 51b are held together via at least one tab or protrusion 68 which each project inwardly from the interior surface of the jaw portion 62 and each mate with a respective recess 70 on the exterior surface of jaw portion 64. When the first and second connector bodies 51a and 51b are connected together, the jaw portion 64 is inserted at least partially into the jaw portion 62 and the protrusions 68 are each received within a respective recess 70. It should be understood that the position of the protrusions 68 on the jaw portion 62 and that of their respective recess 70 on the jaw portion 64 are chosen so that the distal end 53 of the element 52 abuts against the proximal end of the mechanical waveguide 54 when the first and second connector bodies 51a and 51b are secured together. This results in the continuous application of an axial force, in the direction of the longitudinal axis of both waveguides 52 and 54, to the distal end 53 of the element 52 and to the proximal end 53 of the mechanical waveguide 54 in order to ensure that the distal end 53 and the proximal end 55 are maintained in a state of axial compression at all time during use of the connector assembly 50.

While the protrusion 68 projects from the internal face of the jaw portion 62 and the recess 70 is located on the jaw portion 64, it should be understood that the jaw portion 62 may be provided with the recess 70 and the protrusion may project from the jaw portion 64. It should also be understood that the location of the protrusion 68 and/or the location of the recess 70 may vary.

It should be understood that other means may be used for fixedly and removably securing the first and second connector bodies 51a and 51b together. For example, set screws in the jaw portion 62 may apply an inwards radial force onto the exterior surface of jaw portion 64. These set crews may apply a radial force onto the jaw portion 64 into recesses such as 70 on the exterior surface of jaw portion 64.

It should be understood that any adequate means may be used for fixedly and removably secure the first and second connector bodies 51a and 51b while generating an axial compression force on the distal end 53 of the element 52 and the proximal end 55 of the mechanical waveguide 54 to allow the propagation of mechanical waves between the two. For example, the first jaw portion 62 may be a threaded female connector and the second jaw portion 64 may be a threaded male connector threadingly engageable with the jaw portion 62. By screwing the male connector into the female connector, the element 52 and the mechanical waveguide 54 are connected together and an axial force is exerted on their ends 53 and 55, respectively. In another example, the two connector bodies 51a and 51b may mate as in a spring-loaded lock-and-key arrangement common in quick-release connectors, for example as in BNC electrical connectors, push-to-connect pneumatic/hydraulic connectors and quick-turn tubing coupling, such that the jaw portion 62 may be considered as the female/lock component and the jaw portion 64 the male/key component.

In one embodiment and as illustrated in FIG. 5, the connector assembly 50 may further comprise a coupling medium 56 insertable between the distal end 53 of the element 52 and the proximal end 55 of the mechanical waveguide 54. The coupling medium 56 is used to promote the transmission of mechanical waves between the element 52 and the mechanical waveguide 54 with minimal losses. The coupling medium may be a fluid, such as ultrasound gel or glycerine, or a solid such as a metal or polymer like copper or PTFE (Teflon). The coupling medium may be fixedly attached to either the element 52 or the mechanical waveguide 54. For example, a thin disc of PTFE may be glued to the distal end 53 of the element 52.

Figure 6:
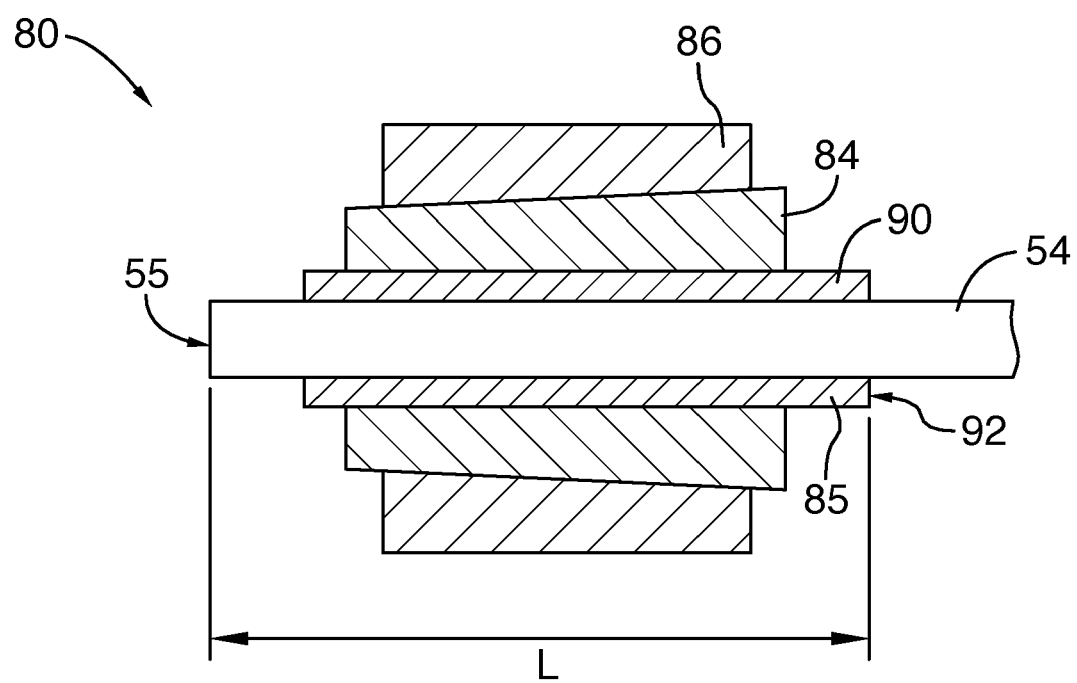
FIG. 6 is a cross-section view of a male connector body comprising an outer jaw portion provided with an inclined internal wall, an inner jaw portion provided with an external inclined wall and a mediating body, in accordance with an embodiment.

FIG. 6 illustrates one embodiment of a connector body 80 which may be in replacement of the second connector body 51b for the connector assembly 50. The connector body 80 is to be secured to a mechanical waveguide 54. The connector body 80 comprises an outer jaw portion 86, an inner jaw portion 84 and a mediating body 85. The outer jaw portion 86 comprises an internal aperture having a frusto-conical shape so that the diameter of the distal end of the internal aperture is greater than the diameter of the proximal end of the internal aperture, i.e. the diameter of the end of the connector body 80 to be connected to another connector in order to secure the proximal end of the mechanical waveguide 54 to another element. The inner jaw portion 84 has an external shape and size that match the size and shape of the internal aperture of the outer jaw portion 86 so that the inner jaw portion 86 be insertable into the internal aperture of the outer jaw portion 86 and in physical contact with the internal wall of the outer jaw portion 86 once inserted therein. In one embodiment and as illustrated in FIG. 6, the longitudinal length of the inner jaw portion 84 is greater than that of the outer jaw portion 86.

The inner jaw portion 84 is also provided with an internal aperture extending along a length thereof and having a cylindrical shape. The internal aperture of the inner jaw portion 84 is sized and shaped to receive the mediating body 85.

The mediating body 85 has an external cylindrical shape and its external diameter is substantially equal to that of the internal aperture of the inner jaw portion 84 so as to be insertable into the internal aperture of the inner jaw portion 84. The mediating body 85 also comprises an internal aperture sized and shaped to receive the mechanical waveguide 54 therein. The internal aperture of the mediating body 85 has a cylindrical shape and its diameter is substantially equal to the diameter of the mechanical waveguide 54. The internal wall of the distal end of the mediating body 85 is bevelled so as to form a countersink 90 at its distal end so ease the insertion of the mechanical waveguide 54 into the internal aperture of the mediating body 85.

During the assembly of the connector body 80, the mediating body 85 is inserted into and fixed to the inside surface of the inner jaw element 84. Then the proximal end 55 of the mechanical waveguide 54 is inserted into the countersink 90 of the mediating body 85 and the mechanical waveguide 54 is pushed into the internal aperture of the mediating body 85 until a desired distance "L" between the proximal end 55 of the mechanical waveguide 54 and the distal end 92 of the mediating body 58 is achieved. Then the outer jaw portion 86 is slid over the inner jaw portion 84 so that the inner jaw portion 84 be inserted into the internal aperture of the outer jaw portion 86. The motion of the outer jaw portion 86 over the conical external wall of the inner jaw portion 84 applies an inwards radial force that compresses the inner jaw portion 84, and subsequently compresses the mediating body 85 onto the mechanical waveguide 54, thereby securing the mechanical waveguide 54 into place within the connector body 80. As mentioned above and once assembled, the connector body 80 may be used in replacement of the connector body 51*b* in the connector assembly 50.

Figure 7:
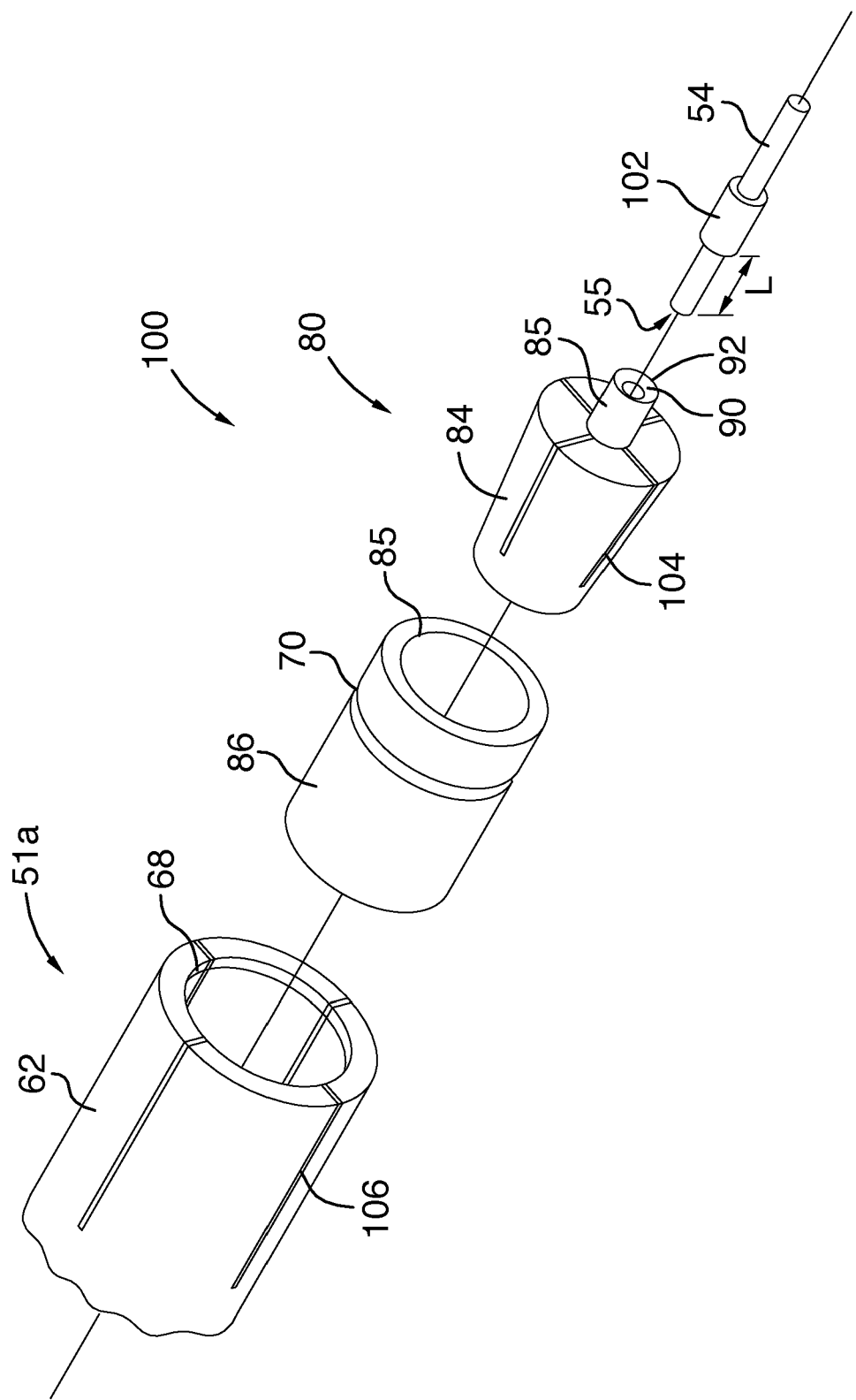
FIG. 7 is an exploded perspective view of a connector assembly comprising a female connector body provided with four slots and a male connector body comprising an outer jaw portion provided with an inclined internal wall, an inner jaw portion provided with an external inclined wall and a mediating body, in accordance with an embodiment.

FIG. 7 illustrates one embodiment of a connector assembly 100 which comprises the connector body 51*a* of the connector assembly 50 and the connector body 80 illustrated in FIG. 6. The connector body 80 corresponds to a female connector body and is sized and shaped so as to be insertable into the connector body 51*a* which corresponds to a female connector body.

In this embodiment, the jaw portion 62 is further provided with four slots 106 which each extend radially through the thickness of the jaw portion 62 and longitudinally from the distal end of the jaw portion 62 towards its proximal end along a given length. It should be understood that the position around the circumference of the jaw portion 62, the number and/or the size of the slots 106 may vary. As a result of the four slots 106, the distal section of the jaw portion 62 is divided into four quarter-cylindrical portions which each may move radially, and the diameter of the internal aperture at the distal end of the jaw portion 62 may vary according to the relative position of the four quarter-cylindrical portions. In other words, the diameter of the opening present at the distal end of the jaw portion 62 may vary to allow the insertion of the connector body 80 in the internal aperture of the jaw portion 62.

In this embodiment, the connector body 80 is further provided with a tubular body 102 which is positioned over the mechanical waveguide 54 to act as a locating or reference marker. The tubular body 102 is provided with an internal cylindrical and longitudinal aperture of which the diameter is substantially equal to the diameter of the mechanical waveguide 54. The mechanical waveguide 54 is inserted into the internal aperture of the tubular body 102 and the tubular body 102 is positioned along the length of the mechanical waveguide 54 so that its proximal end, i.e., the end of the tubular body 102 that faces the proximal end of the mechanical waveguide 54, be positioned at a distance L from the proximal end of the mechanical waveguide 54. It should be understood that the distance L between the proximal end of the mechanical waveguide 54 and the proximal end of the tubular body 102 is substantially identical to the distance L between the distal end 92 of the mediating body 85 and the proximal end of the mechanical waveguide 54 illustrated in FIG. 6. It should be understood that the tubular body 102 is fixedly secured to the mechanical waveguide 54 using any adequate securing method.

While in the illustrated embodiment, the tubular body 102 extends along the while circumference of the mechanical waveguide 54, it should be understood that the tubular body 102 may be shaped so as to extend along only a section of the circumference of the mechanical waveguide 54.

In the embodiment illustrated in FIG. 7, the inner jaw portion 84 is provided with four slots 104 which each extend radially through the thickness of the inner jaw portion 84 and longitudinally along a given section of the length of the inner jaw portion 84 from the distal end thereof. It should be understood that the position around the circumference of the inner jaw portion 84, the number and/or the size of the slots 104 may vary. As a result of the four slots 104, the distal section of the inner jaw portion 84 is divided into four quarter-cylindrical portions which each may move radially, and the diameter of the internal aperture at the distal end of the inner jaw portion 84 may vary according to the relative position of the four quarter-cylindrical portions. In other words, the size of the opening present at the distal end of the inner jaw portion 84 may be increased by spreading the quarter-cylindrical portions one from another to allow the insertion of the mediating body 85 in the internal aperture of the inner jaw portion 84.

In order to assemble the connector assembly 100 illustrated in FIG. 7, the mediating body 85 is inserted into and fixed to the inside surface of the inner jaw element 84. Then the proximal end 55 of the mechanical waveguide 54 is inserted into the countersink 90 of the mediating body 85 and the mechanical waveguide 54 is pushed into the mediating body 85 until the proximal end of the locating marker 102 abuts against the distal end 92 of the mediating body 85, thereby ensuring that the pre-defined distance L between the proximal end 55 of the mechanical waveguide 54 and the distal end 92 of the mediating body 85 is achieved. Then the outer jaw portion 86 is slid over the inner jaw portion 84 so that the inner jaw portion 84 be inserted into the internal aperture of the outer jaw portion 86. The motion of the outer jaw portion 86 over the conical external wall of the inner jaw portion 84 applies an inwards radial force that compresses the inner jaw portion 84, and subsequently compresses the mediating body 85 onto the mechanical waveguide 54, thereby securing the mechanical waveguide 54 into place within the connector body 80. This may be facilitated by the presence of the longitudinal slots 104 through the thickness of the inner jaw element 54 which may increase its radial compliance. Once it has been assembled, the connector body 80 is inserted into the jaw portion 62 of the first connector body 51*a* until the tab 68 of the jaw portion 62 snaps into the recess 70 on the outside surface of the outer jaw element 86.

This assembly may be facilitated by the presence of longitudinal slots 106 through the thickness of the jaw portion 62, which may increase its radial compliance.

Figure 8:
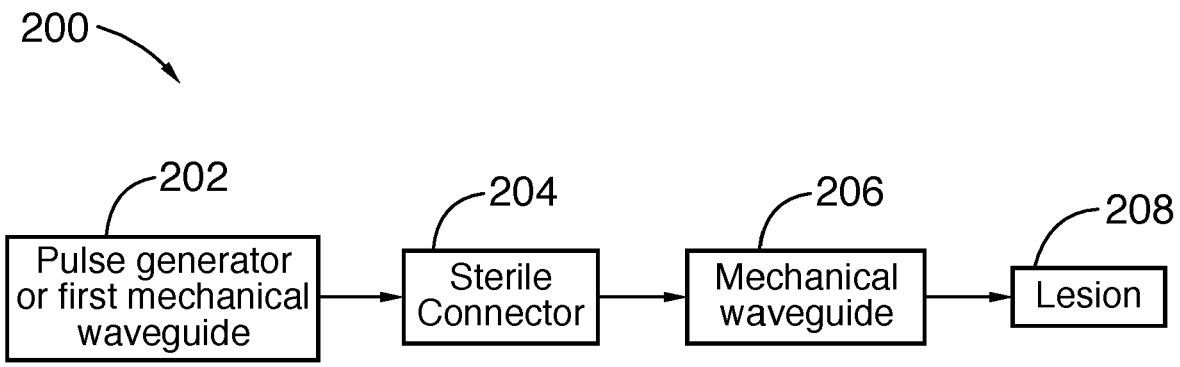
FIG. 8 schematically illustrates a system for generating and delivering mechanical waves or pulses in which two transmission members are connected together via a sterile connector, in accordance with an embodiment.

FIG. 8 illustrates one embodiment of a system 200 for treating a lesion 208 present in a blood vessel of a subject, such as an artery. The system 200 comprises a pulse generator 202, a sterile connector 204 such as the sterile connector described below and a mechanical waveguide 206. It should be understood that the system 200 may comprise a further mechanical waveguide directly connected to the pulse generator 202. In this case, the sterile connector may be used for connecting together the mechanical waveguide 206 and the further mechanical waveguide.

The sterile connector 204 is adapted to connect a first element 202, e.g., the output of a pulse generator or a further mechanical waveguide, to the mechanical waveguide 206, while efficiently coupling mechanical pulses incoming from the first element 202 into the mechanical waveguide 206 and preventing biological contamination from the first element 202 to the mechanical waveguide 206.

Figure 9:
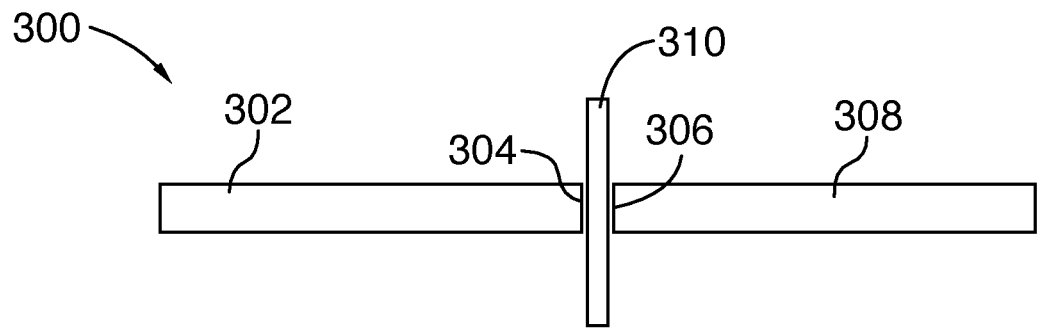
FIG. 9 schematically illustrates two mechanical waveguides coupled together via a sterile barrier, in accordance with an embodiment.

FIG. 9 schematically illustrates one embodiment of a sterile connector 300 used to connect the distal end 304 of a first wave guiding element 302, such as the output of a pulse generator or a mechanical waveguide, to the proximal end 306 of a mechanical waveguide 308. The sterile connector 300 comprises a sterile barrier 310 which separates the distal end 304 of the first member 302 from the proximal end 306 of the mechanical waveguide 308.

The sterile barrier 310 is adapted to prevent biological contamination from the distal end 304 of the first member 302 to be transferred to the proximal end 306 of the mechanical waveguide 308. In this manner, if the mechanical waveguide 308 is sterile, then no contamination from the distal end 304 of the first member 302 is possible and the sterility of the mechanical waveguide 308 can be maintained. The other function of the sterile barrier 310 is to ensure efficient transmission of the mechanical pulses from the distal end 304 of the first member 302 to be transferred to the proximal end 306 of the mechanical waveguide 308. The sterile barrier 310 may also ensure electrical isolation between the two mechanical waveguides 302 and 308.

In one embodiment, the sterile barrier 310 is made from at least one material that can be sterilized and that also provide good acoustic coupling between the material of distal end 304 of the first member 302 and the material of the proximal end 306 of the mechanical waveguide 308. In one embodiment, the good acoustic coupling can be obtained by using a material for the sterile barrier 310 that has a value for acoustic impedance Z (defined as Z=density×speed of sound) as close as possible to the acoustic impedance of the distal end 304 of the first member 302 and that of the proximal end 306 of the mechanical waveguide 308. For example, if both the distal end 304 of the first member 302 and the proximal end 306 of the mechanical waveguide 308 are made of titanium, then the sterile barrier 310 could also be made of titanium which is a sterilizable material. In this case, the sterile barrier has the same acoustic impedance as the distal end 304 of the first member 302 and also as the proximal end 306 of the mechanical waveguide 308, thereby ensuring efficient mechanical energy transmission between the distal end 304 of the first member 302 and the proximal end 306 of the mechanical waveguide 308. In one embodiment, the sterile barrier 310 may be made of a material having an acoustic impedance that is close to that of the mechanical waveguides to promote the transmission of mechanical waves between the mechanical waveguides.

In an embodiment in which the acoustic impedance of the sterile barrier 310 is different from that of the distal end 304 of the first member 302 and the proximal end 306 of the mechanical waveguide 308, then the sterile barrier 310 may be made as thin as possible to prevent or limit transmission losses within the connector. For example the sterile barrier 310 can be made from a thin sterilizable polymer film such as polycarbonate or PTFE.

Figure 10:
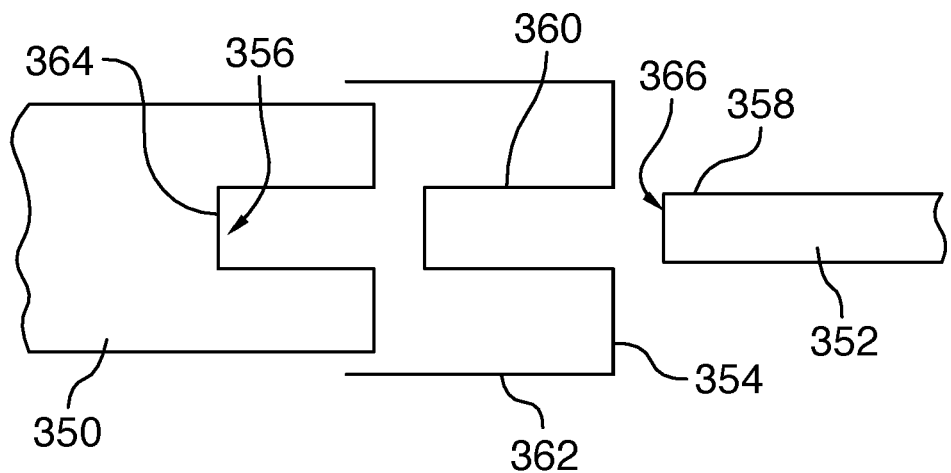
FIG. 10 illustrates a connector assembly comprising a female connector body, a male connector body and a sterile barrier insertable between the female and male connector bodies, in accordance with an embodiment.

FIG. 10 illustrates one embodiment of a sterile connection system which comprises a female portion 350, a male portion 352 and a sterile barrier 354 having a geometry that conforms to the male/female arrangement. The female portion 350 comprises a recess 356 for receiving the male portion 352 therein and the sterile barrier 354 is inserted between the female portion 350 and the male portion 352 into the recess 356 of the female portion so as to prevent any physical contact between the female portion 350 and the male portion 352. The sterile barrier 354 then may act as a sleeve positioned around the proximal end 358 of the male portion 352 to prevent any physical contact between the female and male portions 350 and 352.

In one embodiment, the sterile barrier 354 is flexible and deformable so as to be inserted into the recess 356 of the female portion 350 and cover the part 358 of the male portion 352 that is insertable into the recess 356 of the female portion 352 so as to prevent any physical contact between the female and male portions 350 and 352. In another embodiment, the sterile barrier 354 wraps over the outside surface of the female portion to further prevent any contact between the female portion and the male portion.

In another embodiment, the sterile barrier 354 is rigid. In this case, the sterile barrier 354 has an inner portion 360 that matches the shape of the internal recess 356 so that the sterile barrier 354 may be inserted into the recess 356 of the female portion 350. At the same time, the sterile barrier 354 is provided with an inner portion 360 provided with a shape matching the shape of the proximal end 358 of the male portion 352 for receiving the proximal end 358 of the male portion 352 therein. The sterile barrier 354 also has another portion 362 that can slip over the outside surface of the female portion 350.

In one embodiment, the female and male portions 350 and 352 are part of components adapted to generate and/or propagate mechanical waves. For example, the female portion 350 may be part of or integral with a pulse generator or a first mechanical waveguide while the male portion 352 may be part of or integral with a second mechanical waveguide, or vice versa.

The sterile connection assembly of FIG. 10 provides an adequate alignment between the axis of the female portion 350 and that of the male portion 352 and also provides an adequate angular alignment between the distal face 364 of the female portion 350 and the proximal face 366 of the male portion 352 to prevent or limit losses at the interface therebetween.

Figure 11:
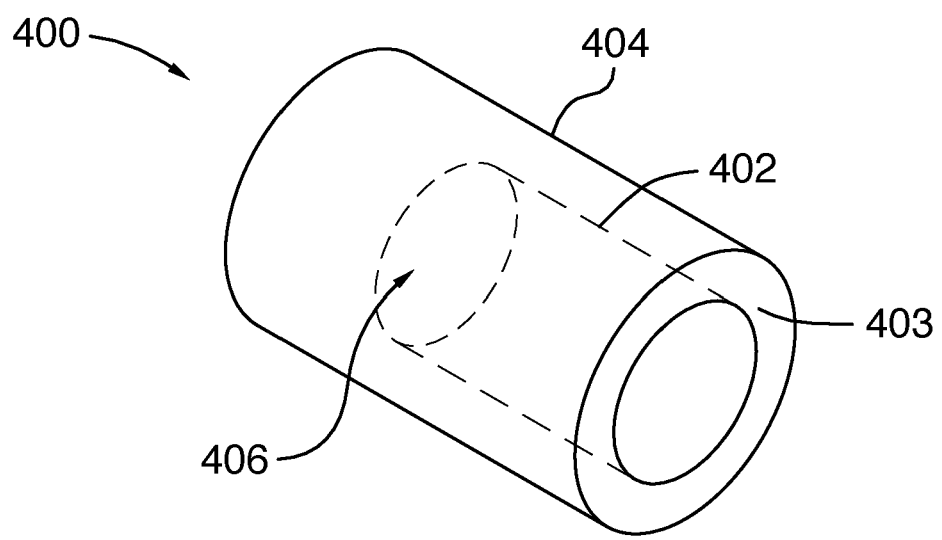
FIG. 11 illustrates a sterile barrier having a tubular shape, in accordance with an embodiment.

FIG. 11 illustrates an embodiment of a sterile barrier 400 that may be used with the connector assembly 50 or 100. The sterile barrier 400 acts as a sleeve for covering the connector body 51*a* in order to isolate the connector body 51*a* from the connector body 51*b* or the connector body 80. The sterile barrier 400 comprises an outer tubular body 404 defining an internal cavity of which the diameter substantially corresponds to the external diameter of the jaw portion 62. The sterile barrier 400 also comprises an inner tubular body 402 inserted in the outer tubular body 404 so that the distal ends of the inner and outer tubular bodies 404 and 402 are coplanar. An annular wall 403 extends between the distal end of the outer tubular body 404 and the distal end of the inner tubular body 402. As a result, the proximal end of the outer tubular body 404 is open while its distal end is closed.

The inner tubular body 402 defines an internal cavity of which the diameter is substantially equal to that of the outer jaw portion 86 and the length of the inner tubular body 402 is at least equal to that of the outer jaw portion 86. The sterile barrier 400 is further provided with a disk-shaped wall 406 which extends at the proximal end of the inner tubular body 402 so as to close the proximal end of the inner tubular body 402.

In order to assemble the connector 100, the connector body 80 is assembled according to the method described above with respect to FIG. 7. Then the sterile barrier 400 is installed over the jaw portion 62 so that the outer tubular body 404 of the sterile barrier 400 be positioned over and around the external face of the jaw portion 62, the annular wall 403 abuts against the distal end of the jaw portion 62 and the inner tubular body 402 be inserted into the internal aperture of the jaw portion 62 along with the wall 406. Once the sterile barrier 400 has been installed over the jaw portion 62, the connector body 80 is secured to the jaw portion 62 by inserting the outer jaw portion 86 into the inner tubular body 402. As a result, the connector body 80 is isolated from the jaw portion 62 so that the connector body 80 and the jaw portion 62 are not in physical contact, and the mechanical waveguides are also isolated. Once the connector 400 has been assembled, the inner tubular body 402 is located between the internal face of the jaw portion 62 and the outer face of the outer jaw portion 86, thereby preventing any physical contact between the connector body 51a and the connector body 80. Furthermore, the wall 406 is located between the ends of the two mechanical waveguides to be connected together, thereby preventing any physical contact between the two mechanical waveguides.

In one embodiment, the sterile barrier 400 is made a flexible and/or deformable material. In this case, the outer and inner tubular bodies 404 and 402 and the wall 406 may be integral.

In another embodiment, the sterile barrier 400 is made of a rigid material.

In one embodiment, the sterile barrier may further act as a coupling medium such as coupling medium 56 in order to promote the transmission of mechanical waves between two mechanical waveguides connected together using the connector assembly 100. In this case, the sterile barrier may be made of a sterilisable material such as titanium, titanium alloy, polycarbonate or PTFE (Teflon™).

By using the above-described sterile barrier with the proper materials and geometry, sterility of the proximal end of a sterile mechanical waveguide used within a minimally-invasive medical treatment device can be maintained throughout the procedure.

In one embodiment, a mediating body may be made of Dow Corning™ 734 RTV Silicone rubber. In another embodiment, a mediating body may be made of Neoprene Rubber Strip.

The embodiments of the invention described above are intended to be exemplary only. The scope of the invention is therefore intended to be limited solely by the scope of the appended claims.

We claim:

1. A connector assembly for connecting together a first mechanical waveguide and a second mechanical waveguide, comprising:
    a first connector body securable to the first mechanical waveguide, the first mechanical waveguide having a constant diameter, the first connector body comprising a first jaw portion provided with a first aperture for receiving the first mechanical waveguide therein;
    a second connector body securable to the second mechanical waveguide, the second mechanical waveguide having the constant diameter, the second connector body comprising a second jaw portion provided with a second aperture for receiving the second mechanical waveguide therein, the first and second connector bodies being removably securable together;
    a first mediating body having an acoustic impedance being lower than an impedance of the first mechanical waveguide, the first mediating body being inserted within the first aperture of the first jaw portion to be positioned between the first jaw portion and the first mechanical waveguide, the first mediating body extending along a circumference of each of the first jaw portion and the first mechanical waveguide; and
    a second mediating body having an acoustic impedance being lower than an impedance of the second mechanical waveguide, the second mediating body being inserted within the second aperture of the second jaw portion to be positioned between the second jaw portion and the second mechanical waveguide, the second mediating body extending along a circumference of each of the second jaw portion and the second mechanical waveguide.

2. The connector assembly of claim 1, wherein one of the first and second connector bodies corresponds to a female connector and another one of the first and second connector bodies corresponds to a male connector being securable within the female connector.

3. A connector assembly for connecting together a first mechanical waveguide and a second mechanical waveguide, comprising:
    a first connector body securable to the first mechanical waveguide, the first connector body comprising a first jaw portion provided with a first aperture for receiving the first mechanical waveguide therein;
    a second connector body securable to the second mechanical waveguide, the second connector body comprising a second jaw portion provided with a second aperture for receiving the second mechanical waveguide therein, the first and second connector bodies being removably securable together;
    a first mediating body having an acoustic impedance being lower than an impedance of the first mechanical waveguide, the first mediating body being inserted within the first aperture of the first jaw portion to be positioned between the first jaw portion and the first mechanical waveguide; and
    a second mediating body having an acoustic impedance being lower than an impedance of the second mechanical waveguide, the second mediating body being inserted within the second aperture of the second jaw portion to be positioned between the second jaw portion and the second mechanical waveguide;
    wherein one of the first and second connector bodies corresponds to a female connector and another one of the first and second connector bodies corresponds to a male connector being securable within the female connector; and
    wherein the second jaw portion is insertable into the first aperture of the first jaw portion so that the second connector body corresponds to the male connector and the first connector body corresponds to the female connector, the connector assembly further comprising a third jaw portion provided with a third aperture for receiving the second mechanical waveguide therein, the third jaw portion being insertable into the second aperture of the second jaw portion.

4. The connector assembly of claim 3, wherein an internal face of the second jaw portion is inclined and the external face of the third jaw portion is inclined to mate the internal face of the second jaw portion.

5. The connector assembly of claim 3, wherein the first jaw portion is provided with at least one slot longitudinally extending from a distal end thereof.

6. The connector assembly of claim 3, wherein the third jaw portion is provided with at least one longitudinally extending slot.

7. The connector assembly of claim 1, wherein the first and second mediating bodies are made of a material being at least one of biocompatible and sterilizable.

8. The connector assembly of claim 1, wherein the first and second mediating bodies are each made of one of rubber and silicon polymer.

9. The connector assembly of claim 1, wherein the first and second mediating bodies are each made of an elastic material.

10. The connector assembly of claim 1, further comprising mechanical means for laterally aligning a distal end of the first mechanical waveguide and a proximal end of the second mechanical waveguide together.

11. The connector assembly of claim 10, wherein the mechanical means comprises an alignment plate comprising an aperture and an inclined plane extending around the aperture, the aperture for receiving therein the distal end of the first mechanical waveguide and the proximal end of the second mechanical waveguide.

12. The connector assembly of claim 1, further comprising mechanical means for angularly aligning a distal end of the first mechanical waveguide and a proximal end of the second mechanical waveguide together.

13. The connector assembly of claim 1, further comprising mechanical means for exerting an axial compressive force between the first and second mechanical waveguides.

14. The connector assembly of claim 13, wherein the mechanical means is adapted to push at least one of the first and second mechanical waveguides towards another one of the first and second mechanical waveguides.

15. The connector assembly of claim 13, wherein the mechanical means comprises at least one of a screw, a lever, an inclined plane, a magnet, and a spring.

16. The connector assembly of claim 1, further comprising mechanical means for exerting a lateral force on the jaw portions.

17. The connector assembly of claim 1, wherein the first and second mediating bodies are each fixedly secured to the first and second mechanical waveguides, respectively, and to the first and second jaw portions, respectively.

18. The connector assembly of claim 17, wherein the first and second mediating bodies are bonded to the first and second mechanical waveguides, respectively, and to the first and second jaw portions, respectively.

19. The connector assembly of claim 17, wherein the first and second mediating bodies are each overmolded to the first and second mechanical waveguides, respectively, and to the first and second jaw portions, respectively.

20. The connector assembly of claim 1, further comprising a coupling medium to be positioned between the first and second mechanical waveguides.

21. The connector assembly of claim 1, further comprising a sterile barrier for preventing a physical contact between the first and second connector bodies and between the first and second mechanical waveguides.

22. The connector assembly of claim 3, further comprising a sterile barrier made of a sterilizable material and insertable between the female and male connectors, the sterile barrier comprising an outer tubular body, an inner tubular body inserted into the outer tubular body, an annular wall extending from a distal end of the outer tubular body to a distal end of the inner tubular body and disk-shaped wall closing a distal end of the inner tubular body, the outer tubular body being positional over an external face of the first jaw portion so that the inner tubular body be insertable into the first aperture of the first jaw portion and the second jaw portion being insertable into the inner tubular body.

23. The connector assembly of claim 22, wherein the sterile barrier is made of a flexible material.

24. The connector assembly of claim 22, wherein the sterile barrier is made of a rigid material.

* * * * *